US006432966B2

(12) United States Patent
Rubin et al.

(10) Patent No.: US 6,432,966 B2
(45) Date of Patent: *Aug. 13, 2002

(54) ANTIVIRAL COMBINATIONS

(75) Inventors: Marc Rubin; Nathaniel A. Brown, both of Chapel Hill; Lynn D. Condreay, Raleigh, all of NC (US); Douglas Fraser Gray, Greenford (GB)

(73) Assignee: SmithKline Beecham Corporation, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 16 days.

(21) Appl. No.: 09/429,863

(22) Filed: Oct. 29, 1999

(51) Int. Cl.$^7$ ................................................ A61K 31/52
(52) U.S. Cl. ........................................ 514/262; 514/274
(58) Field of Search ................................. 514/274, 262

(56) References Cited

U.S. PATENT DOCUMENTS

| | | | | |
|---|---|---|---|---|
| 5,047,407 A | * | 9/1991 | Belleau et al. | ............... 514/274 |
| 5,532,246 A | | 7/1996 | Belleau | |
| 5,859,021 A | * | 1/1999 | Cameron et al. | ............ 514/274 |
| 6,004,968 A | * | 12/1999 | Casey et al. | ................. 514/274 |

FOREIGN PATENT DOCUMENTS

| | | |
|---|---|---|
| EP | 0481 754 B1 | 4/1992 |
| EP | 0481 754 A2 | 4/1992 |
| EP | 0513 917 B1 | 12/1995 |
| WO | WO 91/17159 | 11/1991 |
| WO | WO 92/20344 | 11/1992 |
| WO | WO 95/29174 | 11/1995 |
| WO | WO 96/30025 | 10/1996 |

OTHER PUBLICATIONS

De Clercq, Abstract of International J. of Antimicrobial Agents, vol. 12(2) 81–95, Jul. 1999.*
Yasmanaka et al "Metabolic Studies of BMS–200475 in New Antiviral Compounds", 36th International Conference, Sep. 15–18 1996.*
De Clercq, E., Perspectives for the treatment of hepatitis B virus infections, International Journal of Antimicrobial Agents, 1999, vol. 12, p. 81–95.
Innaimo, S.F., et al., Identifiction of BMS–200475 as a Potent and Selective Inhibitor of Hepatitis B Virus, Antimicrobial Agents and Chemotherapy, Jul. 1997, vol. 41, No. 7, p. 1444–1448.
Seifer, M., et al., In Vitro Inhibition of Hepadnavirus Polymerases by the Triphosphates of BMS–200475 and Lobucavir, Antimicrobial Agents and Chemotherapy, Dec. 1998, vol. 42, No. 12, p. 3200–3208.
Genovesi, E.V., et al., Efficacy of the Carbocyclic 2'–Deoxyguanosine Nucleoside BMS–200475 in the Woodchuck Model of Hepatitis B Virus Infection, Antimicrobial Agents and Chemotherapy, Dec. 1998, vol. 42, No. 12, p. 3209–3217.
Fontana, R.J. et. al., Combination Therapy for Chronic Hepatitis B, Hepatology, Jul. 1997, vol. 26, p. 234–237.
Korba, B.E., In Vitro Evaluation of Combination Therapies against Hepatitis B Virus Replication, Antiviral Research, 1995, vol. 29, p. 49–51.
Colledge, D., et al., In Vitro Antihepadnaviral Activities of Combinations of Penciclovir, Lamivudine and Adefovir, Antimicrobial Agents and Chemotherapy, Mar. 2000, vol. 44, No. 3, p. 551–560.
Loi, A.G., et al., Comparison of Anti–HBV Activity of beta–D and beta–L–DDA–5'–Monophosphate Prodrugs and Effectiveness in Combination with Lamivudine, Nucleosides and Nucleotides, 1999, vol. 18, No. 4, p. 1005–1006.
Colacino, J.M., et al., The Identification and Development of Antiviral Agents for the Treatment of Chronic Hepatitis B Virus Infection, Progress in Drug Research, 1998, vol. 50, p. 259–332.

* cited by examiner

Primary Examiner—James H. Reamer
(74) Attorney, Agent, or Firm—Karen L. Prus

(57) ABSTRACT

The present invention relates to therapeutic combinations comprising (2R,cis)-4-amino-1-(2-hydroxymethyl-1,3-oxathiolan-5-yl)-pyrimidin-2-one (lamivudine) and BMS-200475 which have anti-hepatitis B virus (HBV) activity. The present invention is also concerned with pharmaceutical compositions containing said combinations and their use in the treatment of HBV infections including infections with HBV mutants bearing resistance to nucleoside and/or non-nucleoside inhibitors.

27 Claims, 4 Drawing Sheets

ANTIVIRAL COMBINATIONS

Figure 1:
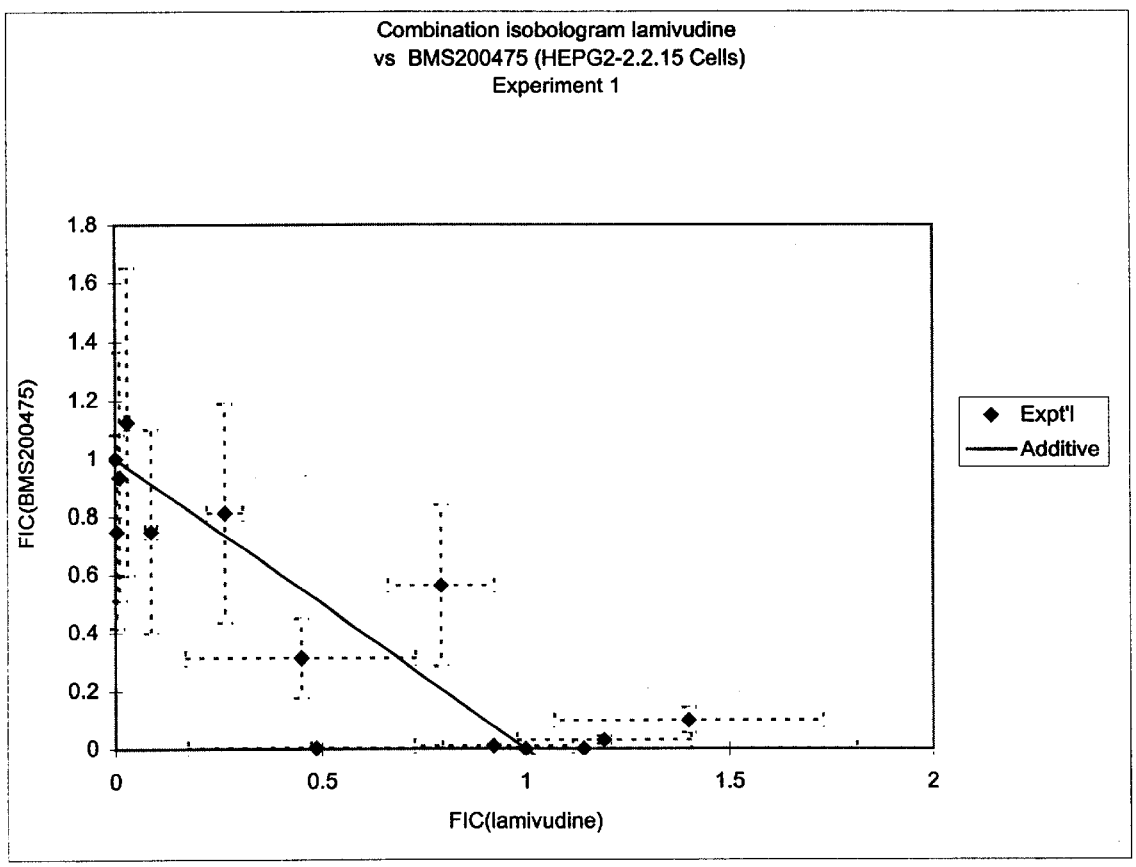

The present invention relates to therapeutic combinations comprising (2R,cis)-4-amino-1-(2-hydroxymethyl-1,3-oxathiolan-5-yl)-pyrimidin-2-one (lamivudine) and BMS-200475, a cyclopentyl guanosine analogue. The present invention is also concerned with pharmaceutical compositions containing said combinations and their use in the treatment of HBV infections including infections with HBV mutants bearing resistance to nucleoside and/or non-nucleoside inhibitors of the replication of the hepatitis B virus.

Hepatitis B is a viral disease transmitted orally or parentally by contaminated material such as blood or blood products, contaminated needles, sexually, and vertically from infected or carrier mothers to their off-spring. In those areas of the world where the disease is common, vertical transmission at an early age results in a high proportion of infected individuals becoming chronic carriers of hepatitis B. An estimated 350 million people world-wide are chronically infected with hepatitis B and as many as 150 million may die from liver disease in the absence of intervention.

Currently, the only established approach to treatment of hepatitis B is repeated injections of interferon, which may be associated with unpleasant side effects, and produces a long lasting response in only one third or less of those treated. Interferon is an immune modulator designed to boost the disease fighting ability of the immune system.

Lamivudine has been reported to be effective against HBV in a two year study, showing that most patients showed substantially reduced levels of viral replication with 52% maintaining undetectable levels of virus thorough to the end of the second year.

The structure of BMS-200475 is as shown in formula (I);

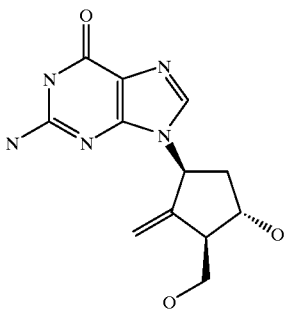

(I)

BMS-200475 has been reported to posses anti-HBV activity in vitro. *Metabolic Studies on BMS-200475, a New Antiviral Compound with Activity Against Hepatitis B Virus.* G Yasmanaka et al. 36th Interscience Conference on Antimicrobial Agents and Chemotherapy Sep. 15–18 1996, New Orleans, La. Oral BMS-200475 has also proved effective against Hepatitis B virus in woodchucks. Safety and pharmacokinetics of BMS-200475 have been studied in both single dose and 14-day multiple dose studies. Abstract 01 DeHertogh D, et al. Second International Conference on Therapies for Viral Hepatitis Kona, Big Island, Hi., Dec. 15–19, 1997.

The use of combinations of the invention may give rise to equivalent antiviral effect with reduced toxicity, or an increase in drug efficacy because synergy between compounds occurs. Lower overall drug doses will also possibly reduce the frequency of occurrence of drug resistant variants of HBV.

We have now found that lamivudine exhibits unexpected advantages when used in combination with BMS-200475. In particular the combinations shows a statistically significant synergistic anti-HBV effect. It is a feature of this invention that the use of this drug combination will provide synergistic antiviral effects, more complete viral suppression, viral suppression over longer periods, limit the emergence of drug resistant HBV mutants and allow better management of drug related toxicites. The use of these drug combinations may also result in a decrease of the number of, for example, tablets administered a day, therefore may increase patient compliance.

As will be appreciated by those skilled in the art, references herein to treatment extend to prophylaxis as well as to the treatment of established infections and symptoms.

Pharmaceutically acceptable salts of lamivudine, and BMS-200475 include those derived from pharmaceutically acceptable inorganic and organic acids. Examples of suitable acids include hydrochloric, hydrobromic, sulphuric, nitric, perchloric, fumaric, maleic, phosphoric, glycollic, lactic, salicylic, succinic, toluene- p-sulphonic, tartaric, acetic, citric, methanesulphonic, formic, benzoic, malonic, naphthalene-2-sulphonic and benzenesulphonic acids. Other acids such as oxalic acid, while not in themselves pharmaceutically acceptable may be useful in the preparation of salts useful as intermediates in obtaining compounds of the invention and their pharmaceutically acceptable acid addition salts.

Salts derived from appropriate bases include alkali metal (e.g. sodium), alkaline earth metal (e.g. magnesium), ammonium and $NR_{4+}$ (where R is $C_{1-4}$ alkyl) salts.

Preferred esters of lamivudine and BMS-200475 are independently selected from the following group: (1) carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$ alkyl, or $C_{1-4}$ alkoxy), or amino; (2) sulphonate esters, such as alkyl- or aralkylsulphonyl (for example, methanesulphonyl); (3) amino acid esters (for example, L-valyl or L-isoleucyl); and (4) phosphonate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group. Any reference to any of the above compounds also includes a reference to a physiologically acceptable salt thereof.

Particularly preferred esters are the mono-, di-, and triphosphate esters of lamivudine and BMS-200475 (both of which may be optionally blocked), or any other compound which upon administration to a human subject is capable of providing (directly or indirectly) said mono-, di-, or triphosphate ester.

Thus according to one aspect, the present invention provides a combination comprising (2R,cis)-4-amino-1-(2-hydroxymethyl-1,3-oxathiolan-5-yl)-pyrimidin-2-one or a pharmaceutically acceptable derivative thereof and BMS-200475 or a pharmaceutically acceptable derivative thereof.

Combinations as described above may herein after be referred to as combinations according to the invention.

As used herein "pharmaceutically acceptable derivative" includes any pharmaceutically acceptable salt, ester or salt of such ester, of lamivudine, BMS-200475 or any other compound which, upon administration to the recipient, is capable of providing (directly or indirectly) such a compound or an antivirally active metabolite or residue thereof.

The present invention further provides combinations according to the invention for use in therapy, particularly in the treatment of an HBV infection including infections resistant to nucleoside and/or non-nucleoside inhibitors of the replication of the hepatitis B virus.

According to another aspect, the present invention provides a method for the treatment of a mammal, including a human, suffering from an HBV infection comprising administration of a therapeutically effective amount of a combination according to the invention.

It will be appreciated that the compounds of the combination may be administered simultaneously, either in the same or different pharmaceutical composition, or sequentially. If there is sequential administration, the delay in administering the second active ingredient should not be such as to lose the benefit of a synergistic therapeutic effect of the combination of the active ingredients. It will also be understood that lamivudine and BMS-200475, or the pharmaceutically acceptable derivatives thereof whether presented simultaneously or sequentially, may be administered individually or in any combination thereof. Lamivudine and BMS-200475 are preferably administered simultaneously or sequentially in separate pharmaceutical formulations, most preferably simultaneously.

Preferably the combination according to the invention is administered as a single combined formulation.

The present invention also provides the use of lamivudine in the manufacture of a medicament for administration simultaneously or sequentially with BMS-200475 for the treatment of HBV infections. It will be appreciated that lamivudine or BMS-200475 may be used in the manufacture of the above medicament.

A further aspect of the invention is a combination according to the invention wherein the lamivudine and BMS-200475 are present in a synergistic ratio.

The synergistic effects of the combination of lamivudine and BMS-200475 or pharmaceutically acceptable derivatives thereof are seen over a ratio, for example, of 200:1 to 2:1 (by weight), preferably 100:1 to 10:1 (by weight).

Conveniently each compound will be employed in the combination in an amount at which it exhibits anti-HBV activity when used alone.

The amount of a combination of lamivudine and BMS-200475 required to be effective as an anti-HBV agent will, of course, vary and is ultimately at the discretion of the medical practitioner. The factors to be considered include the route of administration and nature of the formulation, the animal's body weight, age and general condition and the nature and severity of the disease to be treated.

In general for lamivudine a suitable daily dose will be in the range of from about 0.1 to about 50 mg per kilogram body weight of the recipient per day, preferably in the range of 0.5 to 20 mg per kilogram body weight per day, most preferably in the range of 0.5 to 2 mg per kilogram body weight per day.

The compound is conveniently administered at a level of about 100 mg per day.

For BMS-200475, a suitable daily dose will be in the range of from about 0.02 to about 1 mg per kilogram body weight of the recipient per day, preferably in the range of 0.02 to 0.1 mg per kilogram body weight per day, most preferably in the range of 0.01 to 0.05 mg per kilogram body weight per day.

Unless otherwise indicated all weights of active ingredients are calculated in terms of the drug per se. In the case of a pharmaceutically acceptable derivatives of lamivudine and BSM-200475 or a solvate thereof the figures would be increased proportionately. The desired dose is preferably presented as two, three, four, five, six or more sub-doses administered at appropriate intervals throughout the day. These sub-doses may be administered in unit dosage forms, for example, containing from 1 to 1500 mg, preferably from 5 to 1000 mg, most preferably from 5 to 500 mg of active ingredient per unit dosage form. Alternatively, if the condition of the recipient so requires, the dose may be administered as a continuous infusion.

The components of the combination which may be referred to as active ingredients may be administered for therapy to an animal e.g. a mammal including a human in a conventional manner.

While it is possible for the active ingredients of the combination to be administered as the raw chemical it is preferable to present them as a pharmaceutical composition. Pharmaceutical compositions according to the present invention comprise a combination according to the invention in association with one or more pharmaceutically acceptable carriers or excipients and optionally other therapeutic agents. The carrier(s) must be acceptable in the sense of being compatible with the other ingredients of the formula and not deleterious to the recipient thereof. When the individual components of the combination are administered separately they are generally each presented as a pharmaceutical composition. The references hereinafter to compositions refer unless otherwise stated to compositions containing either the combination or a component thereof.

A combination of lamivudine and BMS-200475 or pharmaceutically acceptable derivatives thereof may conveniently be presented as a pharmaceutical composition with one or more pharmaceutically acceptable carrier thereof in a unitary dosage form. A convenient unitary dosage formulation contains the active ingredients in amounts of from 1 mg to 2 g each, for example, 2 mg to 200 mg such as 25 to 150 mg of lamivudine and 2.5 to 20 mg of BMS-200475.

Pharmaceutical compositions may also be prescribed to the patient in "patient packs" containing the whole course of treatment in a single package, usually a blister pack. Patient packs have an advantage over traditional prescriptions, where a pharmacists divides a patients supply of a pharmaceutical from a bulk supply, in that the patient always has access to the package insert contained in the patient pack, normally missing in traditional prescriptions. The inclusion of a package insert has been shown to improve patient compliance with the physicians instructions.

It will be understood that the administration of the combination of the invention by means of a single patient pack, or patients packs of each composition, within a package insert diverting the patient to the correct use of the invention is a desirable additional feature of this invention.

According to a further aspect of the invention there is provided a patient pack comprising at least one active ingredient of the combination according to the invention and an information insert containing directions on the use of the combination of the invention.

According to another aspect the invention provides a double pack comprising in association for separate administration lamivudine and BMS-200475 or pharmaceutically acceptable derivatives thereof.

Compositions include those suitable for oral, rectal, nasal, topical (including transdermal, buccal and sublingual), vaginal or parenteral (including subcutaneous, intramuscular, intravenous and intradermal) administration. The compositions may conveniently be presented in unit dosage form and may be prepared by any methods well known in the art of pharmacy. Such methods represent a further feature of the present invention and include the step of bringing into association the active ingredients with the carrier which constitutes one or more accessory ingredients. In general, the formulations are prepared by uniformly and intimately bringing into association the active ingredients with liquid carriers or finely divided solid carriers or both, and then if necessary shaping the product.

Compositions of the present invention suitable for oral administration may be presented as discrete units such as capsules, caplets, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Moulded tablets may be made by molding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Preferably the combinations according to the invention are administered orally. Compositions suitable for topical administration in the mouth include lozenges comprising the active ingredients in a flavoured base, usually sucrose and acacia or tragacanth; pastilles comprising the active ingredient in an inert basis such as gelatin and glycerin, or sucrose and acacia; and mouthwashes comprising the active ingredient in a suitable liquid carrier. Compositions for rectal administration may be presented as a suppository with a suitable base comprising, for example, cocoa butter or a salicylate.

Topical administration may also be by means of a transdermal iontophoretic device.

Formulations suitable for vaginal administration may be presented as pessaries, tampons, creams, gels, pastes, foams or spray formulations containing in addition to the active ingredient such carriers as are known in the art to be appropriate.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active combination with the softened or melted carrier(s) followed by chilling and shaping in moulds.

Formulations suitable for parenteral administration include aqueous and nonaqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents; and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Preferred unit dosage formulations are those containing a daily dose or daily subdose of the active ingredients, as herein before recited, or an appropriate fraction thereof.

It should be understood that in addition to the ingredients particularly mentioned above the formulations of this invention may include other agents conventional in the art having regard to the type of formulation in question, for example, those suitable for oral administration may include such further agents as sweeteners, thickeners and flavouring agents.

The compounds of the combination of the present invention may be obtained in a conventional manner.

Methods for the preparation of lamivudine are described in International Patent Applications Numbers. WO91/17159, and WO 95/29174 incorporated herein by reference.

Methods for the preparation of BMS-200475 are described in European Patent No. 0 481 754 incorporated herein by reference.

The following examples are intended for illustration only and are not intended to limit the scope of the invention in any way. "Active ingredient" denotes lamivudine or BMS-200475 or multiples thereof or a physiologically functional derivative of any of the aforementioned compounds.

EXAMPLE 1

Tablet Formulation

The following formulations A, B and C are prepared by wet granulation of the ingredients with a solution of povidone, followed by addition of magnesium stearate and compression.

|  | mg/tablet |
|---|---|
| Formulation A | |
| Active Ingredient A | 100 |
| Active Ingredient B | 5 |
| Lactose B.P. | 105 |
| Povidone B.P. | 7 |
| Sodium Starch Glycollate | 10 |
| Magnesium Stearate | 3 |
|  | 230 |
| Formulation B | |
| Active Ingredient A | 100 |
| Active Ingredient B | 5 |
| Lactose B.P. | 75 |
| Avicel PH 101 | 30 |
| Povidone B.P. | 7 |
| Sodium Starch Glycollate | 10 |
| Magnesium Stearate | 3 |
|  | 230 |

-continued

|  | mg/tablet |
|---|---|
| Formulation C | |
| Active Ingredient A | 100 |
| Active Ingredient B | 5 |
| Lactose B.P. | 100 |
| Starch | 25 |
| Povidone | 2 |
| Magnesium Stearate | 2 |
|  | 234 |

The following formulations, D and E, are prepared by direct compression of the admixed ingredients. The lactose in formulation E is of the direct compression type (Dairy Crest-"Zeparox").

|  | mg/tablet |
|---|---|
| Formulation D | |
| Active Ingredient A | 100 |
| Active Ingredient B | 5 |
| Pregelatinized Starch NF15 | 75 |
|  | 180 |
| Formulation E | |
| Active Ingredient A | 100 |
| Active Ingredient B | 5 |
| Lactose B.P. | 70 |
| Avicel | 50 |
|  | 225 |

Formulation F (Controlled Release Formulation)

The formulation is prepared by wet granulation of the ingredients with a solution of povidone followed by the addition of magnesium stearate and compression.

|  | mg/tablet |
|---|---|
| Active Ingredient A | 100 |
| Active Ingredient B | 5 |
| Hydroxypropylmethylcellulose (Methocel K4M Premium) | 28 |
| Lactose B.P. | 13 |
| Povidone B.P. | 7 |
| Magnesium Stearate | 2 |
|  | 155 |

Drug release takes place over a period of about 6–8 hours and is complete after 12 hours.

EXAMPLE 2

Capsule Formulations

Formulation A

A capsule formulation is prepared by admixing the ingredients of formulation D in Example 1 above and filling into a two-part hard gelatin capsule. Formulation B (infra) is prepared in a similar manner.

|  | mg/capsule |
|---|---|
| Formulation B | |
| Active Ingredient A | 100 |
| Active Ingredient B | 5 |
| Lactose B.P. | 70 |
| Sodium Starch Glycollate | 10 |
| Magnesium Stearate | 1 |
|  | 186 |
| Formulation C | |
| Active Ingredient A | 100 |
| Active Ingredient B | 5 |
| Macrogel 4000 B.P. | 170 |
|  | 275 |

Capsules of formulation C are prepared by melting the Macrogel 4000 B.P., dispersing the active ingredient in the melt and filling the melt into a two-part hard gelatin capsule.

| Formulation D | |
|---|---|
|  | mg/capsule |
| Active Ingredient A | 100 |
| Active Ingredient B | 5 |
| Lecithin | 50 |
| Arachis Oil | 50 |
|  | 205 |

Capsules of formulation D are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b, and c using an extruder, followed by spheronization of the extrudate and drying. The dried pellets are then coated with release-controlling membrane (d) and filled into a two-piece, hard gelatin capsule.

|  |  | mg/capsule |
|---|---|---|
| (a) | Active Ingredient A | 100 |
|  | Active Ingredient B | 5 |
| (b) | Microcrystalline Cellulose | 60 |
| (c) | Lactose B.P. | 60 |
| (d) | Ethyl Cellulose | 6 |
|  |  | 231 |

EXAMPLE 3

Injectable Formulation

| Formulation A | |
|---|---|
|  | mg |
| Active Ingredient A | 100 |
| Active Ingredient B | 5 |

-continued

Formulation A

|  | mg |
|---|---|
| Hydrochloric Acid Solution 0.1 M or Sodium Hydroxide Solution 0.1 M q.s. to pH | 4.0 to 7.0 |
| Sterile water q.s. to | 10 ml |

The active ingredient is dissolved in most of the water (35°–40° C.) and the pH adjusted to between 4.0 and 7.0 with the hydrochloric acid or the sodium hydroxide as appropriate. The batch is then made up to volume with the water and filtered through a sterile micropore filter into a sterile 10 ml amber glass vial (type 1) and sealed with sterile closures and overseals.

Formulation B

| Active Ingredient A | 125 mg |
|---|---|
| Sterile, Pyrogen-free, pH 7 Phosphate Buffer, q.s. to | 25 ml |

EXAMPLE 4

Intramuscular Injection

| Active Ingredient A | 100 mg |
|---|---|
| Active Ingredient B | 5 mg |
| Benzyl Alcohol | 0.067 g |
| Glycofurol 75 | 0.94 g |
| Water for injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

EXAMPLE 5

Syrup

| Active Ingredient A | 100 mg |
|---|---|
| Active Ingredient B | 5 mg |
| Sorbitol Solution | 0.6 g |
| Glycerol | 0.85 g |
| Sodium Benzoate | 0.0025 g |
| Flavour, Peach 17.42.3169 | 0.0125 ml |
| Purified Water q.s. to | 5.00 ml |

The active ingredient is dissolved in a mixture of the glycerol and most of the purified water. An aqueous solution of the sodium benzoate is then added to the solution, followed by addition of the sorbital solution and finally the flavour. The volume is made up with purified water and mixed well.

EXAMPLE 6

Suppository

|  | mg/capsule suppository |
|---|---|
| Active Ingredient A | 100 |
| Active Ingredient B | 5 |
| Hard Fat, B.P. (Witepsol H15 - Dynamit Nobel) | 1770 |
|  | 1875 |

One-fifth of the Witepsol H15 is melted in a steam-jacketed pan at 45° C. maximum. The active ingredient is sifted through a 200 µM sieve and added to the molten base with mixing, using a Silverson fitted with a cutting head, until a smooth dispersion is achieved. Maintaining the mixture at 45° C, the remaining Witepsol H15 is added to the suspension and stirred to ensure a homogenous mix. The entire suspension is passed through a 250 µm stainless steel screen and, with continuous stirring, is allowed to cool to 40° C. At a temperature of 38° C. to 40° C., 2.02 g of the mixture is filled into suitable, 2 ml plastic moulds. The suppositories are allowed to cool to room temperature.

EXAMPLE 7

Pessaries

|  | mg/pessary |
|---|---|
| Active Ingredient A | 100 |
| Active Ingredient B | 5 |
| Anhydrate Dextrose | 160 |
| Potato Starch | 150 |
| Magnesium Stearate | 3 |
|  | 418 |

The above ingredients are mixed directly and pessaries prepared by direct compression of the resulting mixture.

Biological Data

EXAMPLE 8

The human hepatoblastoma cell line (Hep-G2-2.2.15) which constitutively produces infectious HBV was seeded into 96 well microtiter plates at a density of $5 \times 10^3$ cells per well. These cells were treated with a combination of lamivudine (3TC) and BMS-200475 on triplicate plates. Culture media containing drugs was replenished every other day for 9 days, at which time supernatants were collected and analysed for HBV content.

The lamivudine/BMS-200475 combination was tested three times in triplicate in matrix fashion. The 3 experiments utilised a lamivudine range of 100 nM to 0.046 nM (3-fold dilutions in columns). BMS-200475 was serially diluted to form a concentration range of 5.0 to 0.0002 nM, (3.16 fold dilutions in rows). Both drugs were diluted in a separate 96 well microtiter plate, and subsequently transferred onto plates containing the cell monolayers. Cells were grown in 150 µRPMI 1640 supplemented with 2 mM L-Glutamine and 10% fetal bovine serum. Prior to transfer of drug, 120 µl of media was removed from the cells, leaving 30 µl on the monolayers to prevent drying. 90 µl of fresh media without drug was added, followed by the addition of 30 µl of 5× drug dilutions. Lamivudine and BMS-200475 were each tested on their respective plates individually at the same concentrations. Data were normalised to values obtained with non-drug treated cells, and expressed as a percent of control for analysis.

The method used for detection of HBV has been previously described (Jansen R W, Johnson L C, Averett, D R. *High-Capacity in vitro assessment of anti-hepatitis B virus compound selectivity by a virion-specific polymerase chain reaction assay. Antimicrob Agents Chem* 1993; 37 (3): 441–447.). Briefly, HBV detection was performed by "capturing" virus from supernatants on Anti-HBsAg coated plates, washing, denaturing to release HBV DNA, performing PCR with biotinylated primers, streptavidin capture of biotinylated PCR products with concomitant probe hybridization, addition of substrate, and reading optical densities of the calorimetric reaction. Dilutions of a standardised HBV-containing supernatant were included on every plate, and HBV DNA concentrations of test wells were calculated from this HBV standard curve. The useful range of detection is at least 0.045 to 45 fg of HBV DNA, where 30 copies of the genome can be reliably detected. Samples were tested in conjunction with both positive (0.448 fg/ul plasmid DNA) and negative (RPMI medium supplemented with 2 mM L-Glutamine and 10% Fetal calf serum) controls.

The average IC50 and standard error of the IC50s for the triplicate plates were calculated using SAS nonlinear regression to fit data to the Hill equation for each concentration response curve. When only a single determination of an IC50 for a particular dose combination could be made, the average of the standard errors from adjacent concentrations was used to estimate the standard error. Fractional inhibitory concentrations (FIC50) were calculated for each combination and plotted using the isobologram representation (Berenbaum, M.C. (1985) The Expected Effect of a Combination of Agents: the General Solution. J. Theor. Biol. 114, 413–431). To assess statistical significance of synergy or antagonism, an unpaired t-test was used to compare each sum of paired FIC50 values with the theoretical value of 1. P values less than 0.05 were considered statistically significant. In some cases not all concentrations tested could support calculation of an IC50, since response was inhibited to a greater extent than 50 percent of control for all doses.

Figure 2:
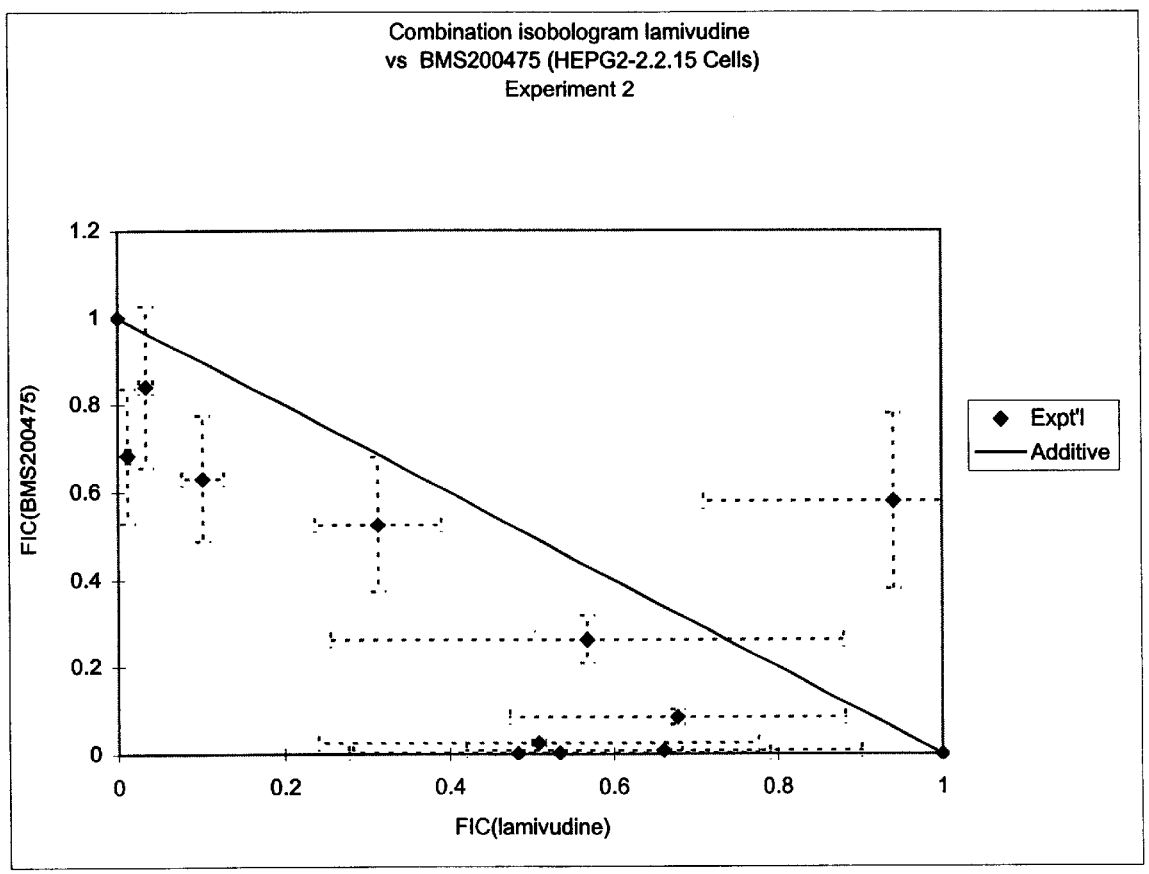
Figure 3:
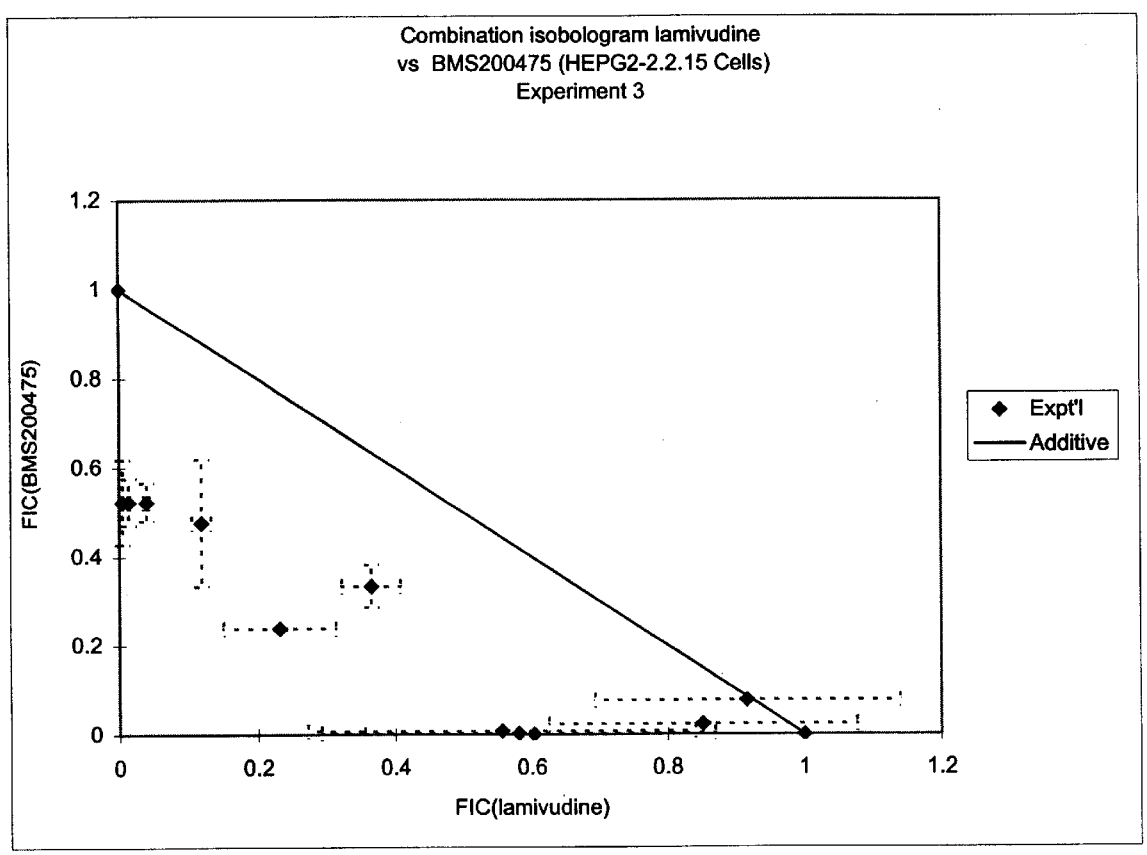

FIGS. 1, 2, and 3 graphically represent the isobologram data for experiments 1, 2, and 3, respectively.

Figure 4:
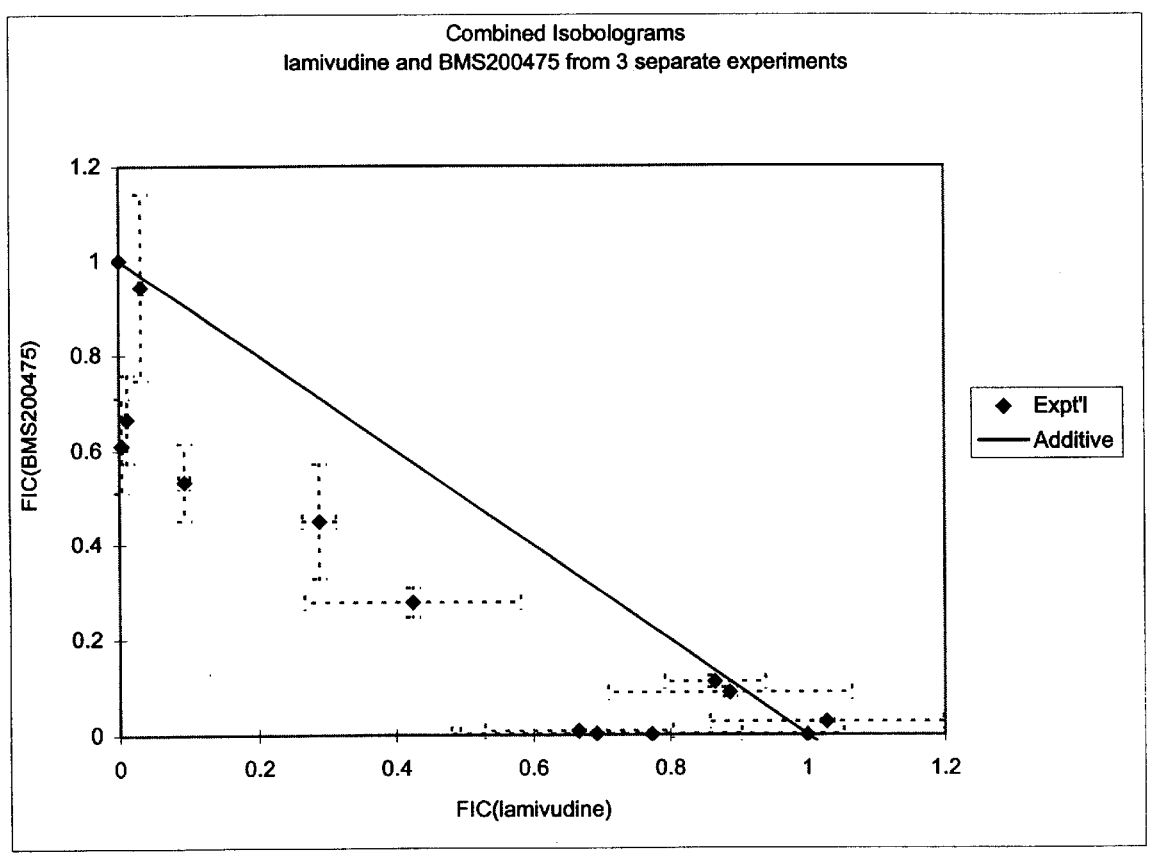

FIG. 4 combines data from all three experiments in a single isobologram.

Interactions with average deviations approaching –0.5 would be considered strong while an observed deviation of –0.2 would be considered weak to moderate. The level of statistical significance indicates that the effect is real and reproducible. Although results from experiment 1 indicated only an additive effect, experiments 2 and 3 each indicated weak but statistically significant synergistic inhibition of HBV replication for the combination of lamivudine and BMS-200475. When data was combined for all three experiments to generate a compiled database, weak but statistically significant synergy was observed.

What is claimed is:

1. A combination comprising (2R,cis)-4-amino-1-(2-hydroxymethyl-1,3-oxathiolan-5-yl)-pyrimidin-2-one or a pharmaceutically acceptable derivative thereof and BMS-200475 or a pharmaceutically acceptable salt or ester derivative thereof wherein (2R,cis)-4-amino-1-(2-hydroxymethyl-1,3-oxathiolan-5-yl)-pyrimidin-2-one and BMS-200475 are present in the range 200:1 to 1:1 by weight of active ingredients.

2. A combination comprising (2R,cis)-4-amino-1-(2-hydroxymethyl-1,3-oxathiolan-5-yl)-pyrimidin-2-one or a pharmaceutically acceptable salt or ester thereof and BMS-200475 or a pharmaceutically acceptable derivative thereof wherein (2R,cis)-4-amino-1-(2-hydroxymethyl-1,3-oxathiolan-5-yl)-pyrimidin-2-one and BMS-200475 are present in the range 100:1 to 10:1 by weight of active ingredients.

3. A pharmaceutical formulation comprising a combination according to claim 1 in association with one or more pharmaceutically acceptable carriers therefor.

4. A formulation according to claim 3 in unit dosage form.

5. A formulation according to claims 3 suitable for oral administration.

6. A formulation according to claim 3 comprising between 25 to 150 mg of lamivudine and 2.5 to 20 mg BMS-200475.

7. A formulation according to claim 3 comprising 100 mg of lamivudine and 5 mg BMS-200475.

8. A pharmaceutical formulation comprising a combination according to claim 2 in association with one or more pharmaceutically acceptable carriers therefor.

9. A formulation according to claim 8 in unit dosage form.

10. A formulation according to claim 8 suitable for oral administration.

11. A formulation according to claim 8 comprising between 25 to 150 mg of lamivudine and 2.5 to 20 mg BMS-200475.

12. A formulation according to claim 8 comprising 100 mg of lamivudine and 5 mg BMS-200475.

13. A method for the treatment of a mammal, including a human, with an HBV infection comprising administration of a therapeutically effective amount of a combination comprising (2R,cis)-4-amino-1-(2-hydroxymethyl-1,3-oxathiolan-5-yl)-pyrimidin-2-one or a pharmaceutically acceptable salt or ester thereof and BMS-200475 or a pharmaceutically acceptable salt or ester thereof.

14. A method as claimed in claim 13 wherein (2R,cis)-4-amino-1-(2-hydroxymethyl-1,3-oxathiolan-5-yl)-pyrimidin-2-one or a pharmaceutically acceptable derivative thereof and BMS-200475 or a pharmaceutically acceptable salt or ester thereof are present in the range 200:1 to 1:1 by weight of active ingredients.

15. A method as claimed in claim 13 wherein (2R,cis)-4-amino-1-(2-hydroxymethyl-1,3-oxathiolan-5-yl)-pyrimidin-2-one or a pharmaceutically acceptable derivative thereof and BMS-200475 or a pharmaceutically acceptable salt or ester thereof are present in the 100:1 to 10:1 by weight of active ingredients.

16. A method according to claim 13 wherein the combination is administered simultaneously.

17. A method according to claim 13 wherein the combination is administered sequentially.

18. A method according to claim 13 wherein the combination is administered as a single combined formulation.

19. A method for the treatment of an HBV infection resistant to nucleoside and/or non-nucleoside inhibitors of the replication of the hepatitis B virus comprising administration of a therapeutically effective amount of a combination comprising (2R,cis)-4-amino-1-(2-hydroxymethyl-1,3-oxathliolan-5-yl)-pyrimidin-2-one or a pharmaceutically acceptable derivative thereof and BMS-200475 or a pharmaceutically acceptable salt or ester thereof.

20. A patient pack comprising of at least one active ingredient selected from (2R,cis)-4-amino-1-(2-hydroxymethyl-1,3-oxathiolan-5-yl)-pyrimidin-2-one, and BMS-200475 and an information insert containing directions on the use of both active ingredients together in combination.

21. A method for the treatment of a mammal, including a human, with an HBV infection comprising administration of a therapeutically effective amount of a synergistic combination comprising (2R,cis)-4-amino-1-(2-hydroxymethyl-1,3-oxathiolan-5-yl)-pyrimidin-2-one or a pharmaceutically acceptable derivative thereof and BMS-200475 or a pharmaceutically acceptable salt or ester thereof.

22. A method as claimed in claim 21 wherein (2R,cis)-4-amino-1-(2-hydroxymethyl-1,3-oxathiolan-5-yl)-pyrimidin-2-one or a pharmaceutically acceptable derivative thereof and BMS-200475 or a pharmaceutically acceptable salt or ester thereof are present in the range 200:1 to 1:1 by weight of active ingredients.

23. A method as claimed in claim 21 wherein (2R,cis)-4-amino-1-(2-hydroxymethyl-1,3-oxathiolan-5-yl)-pyrimidin-2-one or a pharmaceutically acceptable derivative thereof and BMS-200475 or a pharmaceutically acceptable salt or ester thereof are present in the 100:1 to 10:1 by weight of active ingredients.

24. A method according to claim 21 wherein the combination is administered simultaneously.

25. A method according to claim 21 wherein the combination is administered sequentially.

26. A method according to claim 21 wherein the combination is administered as a single combined formulation.

27. A method according to claim 21 for the treatment of an HBV infection resistant to nucleoside and/or non-nucleoside inhibitors of the replication of the hepatitis B virus.

* * * * *